US005900407A

United States Patent [19]

Yerxa et al.

[11] Patent Number: 5,900,407

[45] Date of Patent: May 4, 1999

[54] METHOD OF TREATING DRY EYE DISEASE WITH URIDINE TRIPHOSPHATES AND RELATED COMPOUNDS

[75] Inventors: Benjamin R. Yerxa, Raleigh; Karla M. Jacobus, Cary; William Pendergast, Durham; Janet L. Rideout, Raleigh, all of N.C.

[73] Assignee: Inspire Pharmaceuticals, Inc., Durham, N.C.

[21] Appl. No.: 08/797,472

[22] Filed: Feb. 6, 1997

[51] Int. Cl.[6] .......... A61K 31/70

[52] U.S. Cl. .......... 514/47; 514/51; 514/912

[58] Field of Search .......... 514/47, 50, 51, 514/912

[56] References Cited

U.S. PATENT DOCUMENTS

| | | | |
|---|---|---|---|
| 4,753,945 | 6/1988 | Gilbard et al. . | |
| 4,868,154 | 9/1989 | Gilbard et al. . | |
| 5,292,498 | 3/1994 | Boucher, Jr. .......... | 424/45 |

FOREIGN PATENT DOCUMENTS

| | | |
|---|---|---|
| 23 30 902 | 3/1975 | Germany . |

OTHER PUBLICATIONS

Database Embase Elsevier Science Publishers, Amsterdam NL No. 75036639.

Vovsi, B.M. et al., "Importance of hydrodynamic indices for pathogenic treatment of penetrating wounds of the eye," XP002035486 abstract.

D. Dartt, et al., *Exp. Eye Res.* 67, 27 (1996).

J. Gilbard, et al., *Ophthalmol.* 96, 677 (1978).

J. Gilbard, et al., *Arch. Ophthal.* 109, 672–76 (1991).

J. Gilbard, *CLAO Journal,* 22(2), 141–45 (1996).

J. Gilbard, et al., *Arch. Ophthal.* 112, 1614–16 (1994).

J. Gilbard, et al., *Inv. Ophthal. Vis. Sci.,* 31, 1381–88 (1990).

J. Gromada, et al., *Eur. J. Physiol.* 429, 578 (1995).

G. Grynkiewicz, et al., *J. Biol. Chem.* 260, 3440–3450 (1985).

T. Inatomi, et al., *Inv. Ophthal. Vis. Sci.* 37, 1684 (1996).

M. Lemp, *Cornea* 9(1), S48–S50 (1990).

K. Ng and L.E. Orgel, *Nucleic Acids Res.* 15 (8), 3573–80(1977).

E. Rapaport, et al., *Proc. Natl. Acad. Sci.* USA 78, 838–42 (1981).

I. Sasaki, et al., *Febs Lett.* 264, 130–34 (1990).

I. Sasaki, et al., *J. Physiol.* 447, 103–18 (1992).

P. Vincent, *J. Physiol.* 449, 313–31 (1992).

*Primary Examiner*—Zohreh Fay

*Attorney, Agent, or Firm*—Albert P. Halluin; John A. Bendrick; Howrey & Simon

[57] ABSTRACT

A method and preparation for the stimulation of tear secretion in a subject in need of such treatment is disclosed. The method comprises administering to the ocular surfaces of the subject a purinergic receptor agonist such as uridine 5'-triphosphate [UTP], dinucleotides, cytidine 5'-triphosphate [CTP], adenosine 5'-triphosphate [ATP], or their therapeutically useful analogs and derivatives, in an amount effective to stimulate tear fluid secretion. Pharmaceutical formulations and methods of making the same are also disclosed. Methods of administering the same would include: topical administration via a liquid, gel, cream, or as part of a contact lens or selective release membrane; or systemic administration via nasal drops or spray, inhalation by nebulizer or other device, oral form (liquid or pill), injectable, intra-operative instillation or suppository form.

9 Claims, No Drawings

METHOD OF TREATING DRY EYE DISEASE WITH URIDINE TRIPHOSPHATES AND RELATED COMPOUNDS

INTRODUCTION

Technical Field

This invention relates to a method of regulating secretions in and around the eye of a patient by administering purinergic receptor agonists such as certain uridine, adenine, or cytidine triphosphates as well as other nucleoside phosphate compounds.

BACKGROUND OF THE INVENTION

There are many situations where it is therapeutically desirable to increase the amount of tear fluid produced by the eye. Dry eye disease is the general term for indications produced by abnormalities of the precorneal tear film characterized by a decrease in tear production or an increase in tear film evaporation, together with the ocular surface disease that results. Approximately 38 million Americans are affected with some type of dry eye disorder. Among the indications that are referred to by the general term "dry eye disease" are: keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies (including vitamins), pharmacologic side effects, eye stress and glandular and tissue destruction, environmental exposure to smog, smoke, excessively dry air, airborne particulates, autoimmune and other immunodeficient disorders, and comatose patients rendered unable to blink. The present invention may also be useful as a wash or irrigation solution in conscious individuals, during surgery or to maintain comatose patients or those who cannot blink due to neuromuscular blockade or loss of the eyelids.

A healthy precorneal tear film has several important functions: 1) to protect the cornea from dessication; 2) to aid in the immune response to infections; 3) to enhance oxygen permeation into the cornea; 4) to allow gliding movement of the eyeball and eyelids; and 5) to help maintain the ocular pressure through osmosis. There are two structures responsible for maintaining the properties of the tear film—the lacrimal glands and the conjunctiva (the mucous membrane which surrounds part of the eyeball and inner eyelids). These structures maintain the tear film via regulation of water and electrolyte transport and via mucin release by goblet cells.

The progression of dry eye disease is characterized by four main "milestones". The first milestone is a decrease in tear production. In rabbit models, this decrease in tear production has been shown to correlate with an increase in tear osmolarity. The second milestone is a loss of mucous-containing conjunctival goblet cells. This decrease in goblet cell density becomes evident several weeks after the onset of decreased tear production. The third milestone in the progression of dry eye disease occurs about 1 year later when desquamation of the corneal epithelium is observed. The fourth and last milestone of the disease is a destabilization of the cornea-tear interface (J. Gilbard, *CLAO Journal* 22(2), 141–45 (1996)).

Currently, the pharmaceutical treatment of dry eye disease is mostly limited to administration of artificial tears (saline solution) to temporarily rehydrate the eyes. However, relief is short-lived and frequent dosing is necessary. In addition, artificial tears often have contra-indications and incompatibility with soft contact lenses (M. Lemp, *Cornea* 9(1), S48–S50 (1990)). The use of phosphodiesterase inhibitors, such as 3-isobutyl—1—methylxanthine (IBMX) to stimulate tear secretion is disclosed in U.S. Pat. No. 4,753,945 (applicant intends this and all other patent references to be incorporated herein). The effectiveness of these phosphodiesterase inhibitors is currently being investigated (J. Gilbard, et al., *Arch. Ophthal.* 112, 1614–16 (1994) and 109, 672–76 (1991); idem, *Inv. Ophthal. Vis. Sci.* 31, 1381–88 (1990)). Stimulation of tear secretion by topical application of melanocyte stimulating hormones is described in U.S. Pat. No. 4,868,154.

Thus, as a result of the ineffectiveness and inconvenience of current therapies, medical researchers have sought to develop alternatives for the treatment of dry eye disorders. It has been shown that uridine 5'-triphosphate (UTP) and adenine 5'-triphosphate (ATP) are potent agonists of $P2Y_2$ purinergic receptors found on the surface of human airway epithelium. Activation of these $P2Y_2$ purinergic receptors induces chloride and water secretion, helping hydrate the airway surface secretions. Use of UTP and ATP for the purpose of treating pulmonary disorders characterized by the retention of lung mucus secretions is described in U.S. Pat. No. 5,292,498. Because of the demonstrated ability of UTP to increase hydration of airway epithelial secretions, applicants were motivated to investigate whether UTP and other $P2Y_2$ and $P2Y_4$ purinergic receptor agonists could also stimulate hydration of ocular epithelia. It had previously been shown that P2 type purinergic receptors in rat and mouse lacrimal acinar cells responded to extracellular ATP by increasing intracellular calcium (I. Sasaki, et al., *Febs Lett.* 264, 130–34 (1990); idem, *J Physiol.* 447, 103–18 (1992); P. Vincent, *J Physiol.* 449, 313–31 (1992); J. Gromada, et al., *Eur. J Physiol.* 429, 578 (1995)). Additionally, the same mucin types observed in the human trachea have been observed in the eye (T. Inatomi, et al., *Inv. Ophthal. Vis. Sci.* 37, 1684 (1996)).

Applicant has discovered that tear secretion can be stimulated from lacrimal accessory tissues via $P2Y_2$ and/or $P2Y_4$ purinergic receptor-mediated mechanisms similar to those which hydrate airway epithelia. UTP and other purinergic receptor agonists, administered topically or systemically, provide a novel method of treating dry eye disorders.

SUMMARY OF THE INVENTION

A method of stimulating tear secretion in a subject in need of such treatment is disclosed. The method of the present invention may be used to increase tear production for any reason, including, but not limited to, treatment of dry eye disease. Dry eye disease is defined to include: keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies (including vitamin), pharmacologic side effects, eye stress and glandular and tissue destruction, environmental exposure to smog, smoke, excessively dry air, airborne particulates, autoimmune and other immunodeficient disorders, and comatose patients rendered unable to blink. The present invention may also be useful as a wash or irrigation solution in conscious individuals, during surgery or to maintain comatose patients or those who cannot blink due to neuromuscular blockade, muscle or nerve damage, or loss of the eyelids. The compound uridine triphosphate (UTP) was found to be a potent agonist of $P2Y_2$ and $P2Y_4$ purinergic receptors in lacrimal tissue preparations. Furthermore, an in vivo example in accordance with the invention is conducted on an animal (rabbit) model of dry eye disease.

The method of the present invention comprises topically administering a liquid or gel suspension of $P2Y_2$ and/or $P2Y_4$ purinergic receptor agonists selected from the group consisting of uridine triphosphate [UTP] and its analogs, $P^1P^4$—di(uridine-5') tetraphosphate [$U_2P_4$] and its analogs, cytidine 5'-triphosphate [CTP] and its analogs, and adenosine 5'-triphosphate [ATP], with the particles of UTP, $U_2P_4$, CTP or ATP administered in an amount effective to stimulate tear secretion.

A second aspect of the present invention is the use of a compound of formula I–IV for the manufacture of a medicament for carrying out a therapeutic method of treatment as given above.

A third aspect of the present invention is a pharmaceutical composition comprising a compound of Formula I, II, III or IV, in a pharmaceutical carrier in an amount effective to stimulate tear production in a subject in need of such treatment.

DETAILED DESCRIPTION OF THE INVENTION

The method of the present invention may be used to increase tear production for any reason, including, but not limited to, treatment of dry eye disease. Dry eye disease is defined to include: keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies (including vitamin), pharmacologic side effects, eye stress and glandular and tissue destruction, environmental exposure to smog, smoke, excessively dry air, airborne particulates, autoimmune and other immunodeficient disorders, and comatose patients rendered unable to blink. The present invention may also be useful as a wash or irrigation solution in conscious individuals, during surgery or to maintain comatose patients or those who cannot blink due to muscle or nerve damage, neuromuscular blockade or loss of the eyelids.

Applicant has discovered that uridine 5'-triphosphate (UTP) is a potent agonist for purinergic receptors found in lacrimal gland and conjunctival preparations. The method of the present invention is an improvement upon the current most commonly used treatment of dry eye disease—artificial tears (i.e., saline solution) because UTP stimulates a patient's own tear production and secretion, which maintain natural protective and lubricant characteristics. Furthermore, the method of the present invention may be useful even where lacrimal glands are dysfunctional or absent.

The present invention is concerned primarily with the treatment of human subjects, but may also be employed for the treatment of other mammalian subjects, such as dogs and cats, for veterinary purposes.

The term "uridine triphosphate" as used herein, includes the pharmaceutically acceptable salts thereof, such as (but not limited to) an alkali metal salt such as sodium or potassium; an alkaline earth metal salt such as magnesium or calcium; or an ammonium or tetraalkyl ammonium salt, i.e., $NX_4^+$ (wherein X is $C_{1-4}$ alkyl). Pharmaceutically acceptable salts are salts that retain the desired biological activity of the parent compound and do not impart undesired toxicological effects.

The method of the present invention comprises topically administering a liquid or gel suspension of $P2Y_2$ and/or $P2Y_4$ purinergic receptor agonists selected from the group consisting of general Formula I, i.e., uridine triphosphate [UTP] and its analogs, general Formula II, i.e., $P^1P^4$—di (uridine-5') tetraphosphate [$U_2P_4$] and its analogs, general Formula III, i.e., cytidine 5'-triphosphate [CTP] and its analogs, and general Formula IV, i.e., adenosine 5'-triphosphate [ATP] and its analogs, with the particles of Formula I, II, III or IV administered in an amount effective to stimulate tear secretion.

Active Compounds of the Invention

UTP and its analogs are depicted in general Formula I:

Formula I

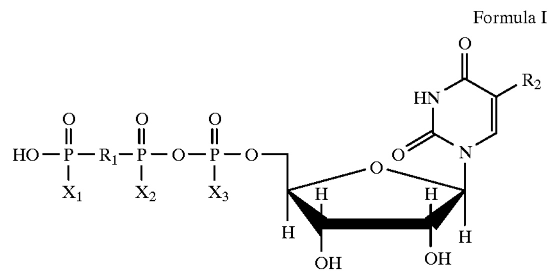

wherein:

$X_1$, $X_2$ and $X_3$ are each independently either $O^-$ or $S^-$. Preferably, $X_2$ and $X_3$ are $O^-$.

$R_1$ is O, imido, methylene or dihalomethylene (e.g., dichloromethylene or diflouromethylene). Preferably, $R_1$ is oxygen or difluoromethylene.

$R_2$ is H or Br. Preferably, $R_2$ is H. Particularly preferred compounds of Formula I are uridine 5'-triphosphate (UTP) and uridine 5'—O—(3-thiotriphosphate) (UTPγS).

A dinucleotide is depicted by the general Formula II:

Formula II

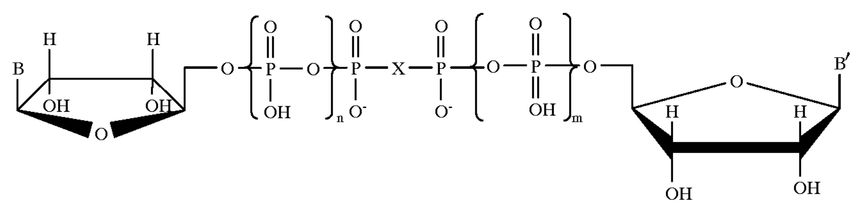

wherein:

X is oxygen, imido, methylene or difluoromethylene;

n=0 or 1;

m=0 or 1;

n+m=0, 1 or 2; and

B and B' are each independently a purine residue or a pyrimidine residue linked through the 9- or 1-position, respectively. In the instance where B and B' are uracil, attached at the N−1 position to the ribosyl moiety, then the total of m+n may equal 3 or 4 when X is oxygen. The ribosyl moieties are in the D-configuration, as shown, but may be L-, or D- and L-. The D- configuration is preferred.

B and B' are each independently a purine residue, as in Formula IIa, or a pyrimidine residue, as in Formula IIb, linked through the 9- or 1-position, respectively. In the instance where B and B' are uracil, attached at the N-1 position to the ribosyl moiety, then the total of m+n may equal 3 or 4 when X is oxygen. The ribosyl moieties are in the D-configuration, as shown, but may be L-, or D- and L-. The D-configuration is preferred.

Formula IIa

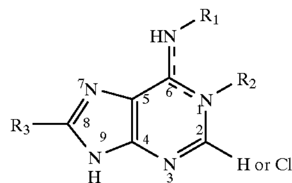

The substituted derivatives of adenine include adenine 1-oxide; 1,N6-(4- or 5-substituted etheno) adenine; 6-substituted adenine; or 8- substituted aminoadenine, where R' of the 6- or 8-HNR' groups are chosen from among: arylalkyl ($C_{1-6}$) groups with the aryl moiety optionally functionalized as described below; alkyl; and alkyl groups with functional groups therein, such as: ([6-aminohexyl]carbamoylmethyl)-, and ω-acylated-amino(hydroxy, thiol and carboxy) derivatives where the acyl group is chosen from among, but not limited to, acetyl, trifluroroacetyl, benzoyl, substituted-benzoyl, etc., or the carboxylic moiety is present as its ester or amide derivative, for example, the ethyl or methyl ester or its methyl, ethyl or benzamido derivative. The w-amino(hydroxy, thiol) moiety may be alkylated with a $C_{1-4}$ alkyl group.

Likewise, B or B', or both may be a pyrimidine with the general formula of FIG. IIb, linked through the 1-position:

Figure IIb

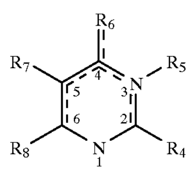

wherein:

$R_4$ is hydroxy, mercapto, amino, cyano, aralkoxy, $C_{1-6}$ alkoxy, $C_{1-6}$ alkylamino and dialkylamino, the alkyl groups optionally linked to form a heterocycle;

$R_5$ is hydrogen, acyl, $C_{1-6}$ alkyl, aroyl, $C_{1-5}$alkanoyl, benzoyl, or sulphonate;

$R_6$ is hydroxy, mercapto, alkoxy, aralkoxy, $C_{1-6}$-alkylthio, $C_{1-5}$ disubstituted amino, triazolyl, alkylamino or dialkylamino, where the alkyl groups are optionally linked to form a heterocycle or linked to $N^3$ to form an optionally substituted ring;

$R_7$ is hydrogen, hydroxy, cyano, nitro, alkenyl, with the alkenyl moiety optionally linked through oxygen to form a ring optionally substituted on the carbon adjacent to the oxygen with alkyl or aryl groups, substituted alkynyl or hydrogen where $R^8$ is amino or substituted amino and halogen, alkyl, substituted alkyl perhalomethyl (e.g., $CF_3$), $C_{2-6}$ alkyl, $C_{2-3}$ alkenyl, or substituted ethenyl (e.g., allylamino, bromvinyl and ethyl propenoate, or propenoic acid), $C_{2-3}$ alkynyl or substituted alkynyl when $R_6$ is other than amino or substituted amino and together $R_5$–$R_6$ may form a 5 or 6-membered saturated or unsaturated ring bonded through N or O at $R_6$, such a ring may contain substituents that themselves contain functionalities;

$R_8$ is hydrogen, alkoxy, arylalkoxy, alkylthio, arylalkylthio, carboxamidomethyl, carboxymethyl, methoxy, methylthio, phenoxy or phenylthio.

In the general structure of FIG. IIb above, the dotted lines in the 2- to 6-positions are intended to indicate the presence of single or double bonds in these positions; the relative positions of the double or single bonds being determined by whether the $R_4$, $R_6$ and $R_7$ substituents are capable of keto-enol tautomerism.

In the general structures of FIGS. IIa and IIb above, the acyl groups advantageously comprise alkanoyl or aroyl groups. The alkyl groups advantageously contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above mentioned alkenyl and alkynyl groups advantageously contain 2 to 8 carbon atoms, particulary 2 to 6 carbon atoms, e.g., ethenyl or ethynyl, optionally substituted by one or more appropriate substituents as described below. Appropriate substituents on the above-mentioned alkyl, alkenyl, alkynyl, and aryl groups are advantageously selected from halogen, hydroxy, $C_{1-4}$ alkoxy, $C_{1-4}$ alkyl, $C_{6-12}$ arylalkoxy, carboxy, cyano, nitro, sulfonamido, sulfonate, phophate, sulfonic, amino and substituted amino wherein the amino is singly or doubly substituted by a $C_{1-4}$ alkyl, and when doubly substituted, the alkyl groups optionally being linked to form a heterocycle.

CTP and its analogs are depicted by general Formula III:

Formula II

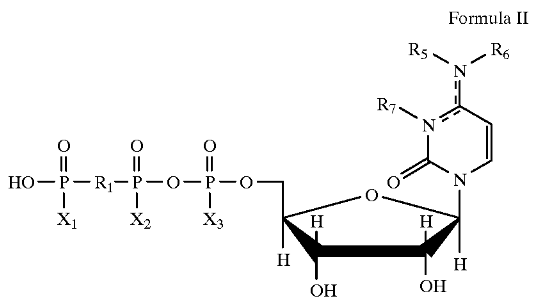

wherein:

$R_1$, $X_1$, $X_2$ and $X_3$ are defined as in Formula I.

$R_5$ and $R_6$ are H while $R_7$ is nothing and there is a double bond between N-3 and C-4 (cytosine), or $R_5$, $R_6$ and $R_7$ taken together are —CH=CH—, forming a ring from N-3 to N-4 with a double bond between N-4 and C-4 (3,$N^4$-ethenocytosine) optionally substituted at the 4- or 5-position of the etheno ring.

ATP and its analogs are depicted by general Formula IV:

Formula IV

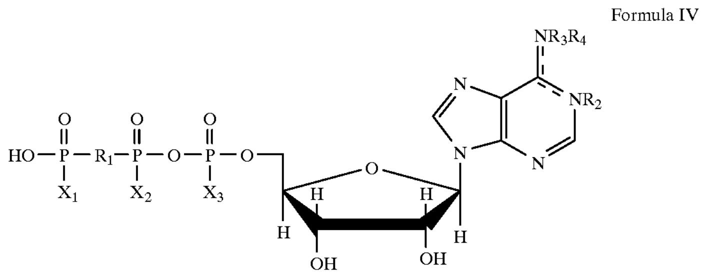

wherein:

$R_1$, $X_1$, $X_2$ and $X_3$ are defined as in Formula I.

$R_3$ and $R_4$ are H while $R_2$ is nothing and there is a double bond between N-1 and C-6 (adenine), or $R_3$ and $R_4$ are H while $R_2$ is O and there is a double bond between N-1 and C-6 (adenine 1-oxide), or $R_3$, $R_4$ and $R_2$ taken together are —CH═CH—, forming a ring from N-6 to N-1 with a double bond between N-6 and C-6 (1,N6-ethenoadenine).

For simplicity, Formulae I, II, III and IV herein illustrate the active compounds in the naturally occurring D-configuration, but the present invention also encompasses compounds in the L-configuration, and mixtures of compounds in the D- and L- configurations, unless otherwise specified. The naturally occurring D-configuration is preferred.

The active compounds of the invention may also be present in the form of the their pharmaceutically acceptable salts, such as, but not limited to, an alkali metal salt such as sodium or potassium; an alkaline earth metal salt such as manganese, magnesium or calcium; or an ammonium or tetraalkyl ammonium salt, i.e., $NX_4^+$ (wherein X is $C_{1-4}$). Pharmaceutically acceptable salts are salts that retain the desired biological activity of the parent compound and do not impart undesired toxicological effects.

Methods of Administration

The active compounds disclosed herein may be administered to the eyes of a patient by any suitable means, but are preferably administered by administering a liquid or gel suspension of the active compound in the form of drops, spray or gel. Alternatively, the active compounds may be applied to the eye via liposomes. Further, the active compounds may be infused into the tear film via a pump-catheter system. Another embodiment of the present invention involves the active compound contained within a continuous or selective-release device, for example, membranes such as, but not limited to, those employed in the Ocusert™ System (Alza Corp., Palo Alto, Calif. ). As an additional embodiment, the active compounds can be contained within, carried by, or attached to contact lenses which are placed on the eye. Another embodiment of the present invention involves the active compound contained within a swab or sponge which can be applied to the ocular surface. Another embodiment of the present invention involves the active compound contained within a liquid spray which can be applied to the ocular surface.

The quantity of the active compound included in the topical solution is an amount sufficient to achieve dissolved concentrations of the active compound on the ocular surface of the subject of from about $10^{-7}$ to about $10^{-1}$ Moles/liter, and more preferably from about $10^{-6}$ to about $10^{-1}$ Moles/liter.

Depending upon the solubility of the particular formulation of active compound administered, the daily dose to promote tear secretion may be divided among one or several unit dose administrations. The total daily dose for UTP (for example) may range from 0.25 mg/ml to 50 mg/ml, depending upon the age and condition of the subject. A currently preferred unit dose for UTP is about 1 to 100 milligrams given at a regimen of 2 to 6 administrations per day.

Some compounds of Formula I, III and IV can be made by methods which are well known to those skilled in the art; some are commercially available, for example, from Sigma Chemical Company, PO Box 14508, St. Louis, Mo. 63178. Compounds of Formula II can be made in accordance with known procedures, or variations thereof which will be described by: P. Zamecnik, et al., *Proc. Natl. Acad. Sci. U.S.A* 89, 838–42 (1981); and K. Ng and L. E. Orgel. *Nucleic Acids Res.* 15(8), 3572–80 (1977).

The topical solution containing the active compound may also contain a physiologically compatible vehicle, as those skilled in the ophthalmic art can select using conventional criteria. The vehicles may be selected from the known ophthalmic vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In addition to the topical method of administration described above, there are various methods of administering the active compounds of the present invention systemically. One such means would involve an aerosol suspension of respirable particles comprised of the active compound, which the subject inhales. The active compound would be absorbed into the bloodstream via the lungs or contact the lacrimal tissues via nasolacrimal ducts, and subsequently contact the lacrimal glands in a pharmaceutically effective amount. The respirable particles may be liquid or solid, with a particle size sufficiently small to pass through the mouth and larynx upon inhalation; in general, particles ranging from about 1 to 10 microns, but more preferably 1–5 microns, in size are considered respirable.

Another means of systemically administering the active compounds to the eyes of the subject would involve administering a liquid/liquid suspension in the form of eye drops or eye wash or nasal drops of a liquid formulation, or a nasal spray of respirable particles which the subject inhales. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing compounds of Formula I, II, III or IV are in the form of tablets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Additional means of systemic administration of the active compound to the eyes of the subject would involve a suppository form of the active compound, such that a therapeutically effective amount of the compound reaches the eyes via systemic absorption and circulation.

Further means of systemic administration of the active compound would involve direct intra-operative instillation of a gel, cream, or liquid suspension form of a therapeutically effective amount of the active compound.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The invention is illustrated further by the following examples which are not to be construed as limiting the invention in scope or spirit to the specific procedures described in it. In vivo examples in accordance with the invention are conducted on rabbits with dry eyes. The dry eye disorder is created by surgically closing the duct that carries fluid from the main lacrimal gland to the tear film and surgically removing the nictitans and harderian glands. It is recognized by those skilled in the art that results of ophthalmologic tests carried out on the aforementioned rabbit model have close correlation with humans afflicted with dry eye disease, and, therefore, the results provide an accurate prediction of therapeutic efficacy in humans.

EXAMPLE 1

Stimulation of Mucin Release in Rat Conjunctival Preparations

Male, Sprague-Dawley rats at 12 weeks of age (Charles River Laboratories, Wilmington, Mass.) are sacrificed by intraperitoneal injection of sodium pentobarbital (1300 mg/kg) and a 20$\mu$L drop of 1% lidocaine diluted with tear buffer (106.5 mM NaCl, 26.1 mM $NaHCO_3$, 18.7 mM KCl, 1.0 mM $MgCl_2$, 0.5 mM $NaH_2PO_4$, 1.1 mM $CaCl_2$, and 10 mM HEPES pH 7.45) is placed on the ocular surface for 10 min. The inferior conjunctiva extending from lid to cornea and medial to lateral canthus is removed from each eye and placed on filter paper. Each conjunctiva is cut in half longitudinally and the four resulting pieces are incubated in keratinocyte growth medium (Clonetics Corp., San Diego, Calif.) with or without agonist for 1 hr at 4° C. in half strength Karnovsky's solution (2.5% glutaraldehyde and 2% paraformaldehyde in cacodylate buffer, pH 7.4), embedded in methacrylate, and sectioned into 3 $\mu$m pieces. Six sections from each piece of tissue are stained with Alcian Blue (pH 5) and periodic acid-Schiff's reagent (AB-PAS). The number of mucin-containing goblet cells in each section is counted in masked fashion using light microscopy (standard microscope with a square indexed eye piece reticule) at 160 × magnification. In unstimulated conjunctival tissue culture the goblet cells have defined borders and are intensely stained due to the mucin-containing secretory granules in the apical portion of each goblet cell. Upon stimulation the mucin granules are released into the medium. The number of quiescent mucin-containing goblet cells per unit area (0.16 $mm^2$) is counted and averaged. A decrease in the number of mucin-containing goblet cells per unit area indicate an increase in mucin secretion, because the staining is caused by non-secreted cells. Data are expressed as the mean percentage of the value from the control (untreated) tissue. The method of this example is adapted from D. Dartt, et al., *Exp. Eye Res.,* 63, 27 (1996), which is incorporated herein by reference.

EXAMPLE 2

Measurement of Intracellular Calcium

Rat conjunctival cells grown on vitrogen coated coverslips are loaded with a final concentration of 3 $\mu$M Fura-2/AM at 37° C. for 30 min. The cells are then washed in NaCl ringer and mounted in a chamber for measurement of fluorescence. To reduce the rate of leakage of Fura-2 from the cell into the extracellular space and avoid time-dependent compartmentalization of the probe, all measurements of $[Ca^{2+}]_i$ are conducted at 25° C. At this temperature, no vesicular bright spots indicative of compartmentalization of the probe are observed.

Measurements of $[Ca^{2+}]_i$ in single rat conjunctival epithelial cells are obtained with a modular microspectrofluorometer (SPEX Industries, Inc., Edison, N.J.) attached to a Zeiss Axiovert IM 35 microscope. The system is equipped with a xenon lamp, beam splitter, two monochromators and a rotating chopper mirror that permit excitation of cell fluorescence at alternating wavelengths of 340 and 380 nm (emission>450 nm). The fluorescent signal from a single cell is measured with a photometer equipped with a pinhole (spot diameter of 3–5 $\mu$m) that exclude signals from adjacent cells.

After agonist is added, the fluorescent signal is quenched by a NaCl ringer solution containing $1.5\times10^{-4}$M digitonin and $10^{-3}$M $MnCl_2$. The remaining signal at each excitation wavelength, equivalent to the background fluorescence in non-loaded cells, is subtracted from data from Fura-2/AM loaded cells before the ratio (340/380 nm) is taken. The 340 nm/380 nm ratio is converted to an actual $[Ca^{2+}]_i$ measurement by using the external calibration standards and the formula derived by G. Grynkiewicz, et al. (*J. Biol. Chem.* 260, 3440–3450 (1985)), used with dual wavelength measurements: $[Ca^{2+}]_i$=K $[(R_x-R_o)/(-R_s-R_x)]$, with $R_o$ and $R_s$ representing the ratios at zero $Ca^{2+}$ and saturating $Ca^{2+}$, respectively. $R_x$ represents the experimental ratio. K is $K_d/(F_o/F_s)$, with $K_d=1.57\times10^{-7}$M at 25° C. as the effective dissociation constant for Fura-2, and $F_o$ and $F_s$ represent the fluorescence intensities at 380 nm with zero and saturating $Ca^{2+}$, respectively. The method of this example is adapted from R. Boucher, et al., U.S. Pat. No. 5,292,498, which is incorporated herein by reference.

EXAMPLE 3

Reversing the Onset of Dry Eye Disease in Rabbit Model for KCS

Keratoconjunctivitis sicca (KCS) is created in the right eyes of 8 New Zealand white rabbits by surgically closing the lacrimal gland excretory duct, and removing the nictitating membrane, nictitans gland and Harderian gland. All rabbits are left untreated for 8 weeks and KCS is confirmed by measuring elevated tear film osmolarity by taking 0.1–0.4 $\mu$L tear samples as previously described (J. Gilbard, et al., *Ophthalmol.* 96, 677 (1978)). A 3.0 mmol solution of UTP or analog is prepared in a preserved, isotonic buffer solution. Four of the rabbits are treated with 1 drop (10 $\mu$L) UTP or analog solution four times a day, excluding weekends. The remaining 4 untreated rabbits serve as controls. After treatment began, 0.1–0.4 $\mu$L tear samples are taken from all rabbits for osmolarity measurements on Monday mornings before the first dose. At 20 weeks the animals are sacrificed and goblet cell densities are measured by staining with alcian blue and periodic acid-Schiff's reagent (D. Dartt, et al., *Exp. Eye Res.* 67, 27 (1996)).

The study is designed to demonstrate that UTP and analogs decrease elevated tear film osmolarity and increased conjunctival goblet cell densities, thus reversing the onset of occular surface disease in a rabbit model for KCS. The method of this example is adapted from J. P. Gilbard, *Arch. Ophthalmol.* 112, 1614 (1994), which is incorporated herein by reference.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of stimulating tear secretion from lacrimal tissues comprising the step of administering to the eyes an effective amount of a preparation which includes a compound that activates the purinergic receptors in the lacrimal tissues of a subject in need of such treatment, said compound selected from a group consisting of: uridine 5'-triphosphate as described by Formula I, dinucleotides as described by Formulae II, III and IV, cytidine 5'-triphosphate triphosphate as described by Formula V, adenosine 5"-triphosphate as described by Formula VI and their active analogs and derivatives;

Formula I

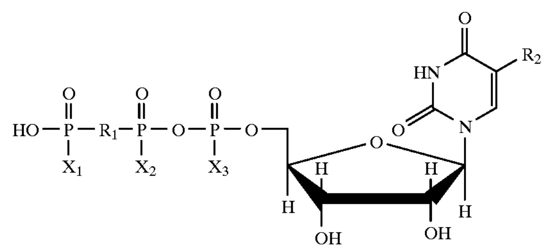

wherein:

$X_1$, $X_2$ and $X_3$ are each independently selected from the group consisting of $O^-$ and $S^-$;

$R_1$ is selected from the group consisting: of O, imido, methylene and dihalomethylene;

$R_2$ is selected from the group consisting of H and Br;

Formula II

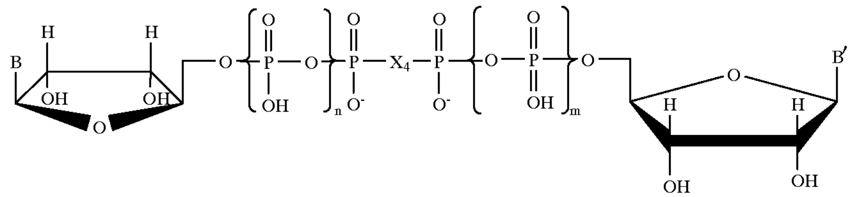

wherein:

$X_4$ is selected from the group consisting of:
(a) oxygen
(b) imido,
(c) methylene and
(d) difluoromethylene;

n=0 or 1;
m=0 or 1;
n+m=0, 1 or 2; and

B and B' are each independently a purine residue, as in Formula III, or a pyrimidine residue, as in Formula IV, linked through the 9- or 1 - position, respectively;

Formula III

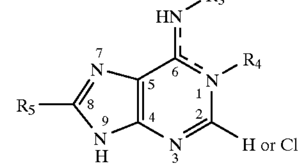

wherein $R_4$ is O or is absent; or $R_3$ and $R_4$ taken together may for optionally substituted 5-membered fused inidazole ring; 1or $R_3$ of the 6-$HNR_3$ group or $R_5$ of the 8-$HNR_5$ group is selected from the group consisting of:

(a) arylalkyl ($C_{1-6}$) groups with the aryl moiety optionally substituted,
(b) alkyl,
(c) (carbamoylmethyl),
(d) ω-amino alkyl ($C_{2-10}$),
(e) ω-hydroxy alkyl ($C_{2-10}$),
(f) ω-thiol alkyl ($C_{2-10}$),
(g) ω-carboxy alkyl ($C_{2-10}$),
(h) the ω-acylated derivatives of (b), (c) or (d) wherein the acyl group is either acetyl, trifluroacetyl, benzoyl, or substituted-benzoyl alkyl($C_{2-10}$), and
(i) ω-carboxy alkyl ($C_{2-10}$) as in (e) above wherein the carboxylic moiety is an ester or an amide;

Formula IV

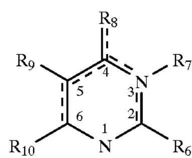

wherein:

$R_6$ is selected from the group consisting of:

(a) hydroxy,
(b) mercapto,
(c) amino,
(d) cyano,
(e) aralkoxy,
(f) $C_{1-6}$ alkylthio,
(g) $C_{1-6}$ alkoxy,
(h) $C_{1-6}$ alkylamino and
(i) dialkylamino, wherein the alkyl groups of said dialkylamino are optionally linked to form a heterocycle;

$R_7$ is selected from the group consisting of:

(a) hydrogen,
(b) acyl,
(c) $C_{1-6}$ alkyl,
(d) aroyl,
(e) $C_{1-5}$
(f) alkanoyl,
(g) benzoyl and
(h) sulphonate;

$R_8$ is selected from the group consisting of:

(a) hydroxy,
(b) mercapto,
(c) alkoxy,
(d) aralkoxy,
(e) $C_{1-6}$ -alkylthio,
(f) $C_{1-5}$ disubstituted amino,
(g) triazolyl,
(h) alkylamino and
(i) dialkylamino, wherein the alkyl groups of said dialkylamino are optionally linked to form a heterocycle or linked to $N^5$ to form an optionally substituted ring;

$R_7$ –$R_8$ together forms a 5 or 6-membered saturated or unsaturated ring bonded through N or O at $R_8$, wherein said ring is optionally substituted, $R_9$ is selected from the group consisting of:

(a) hydrogen,
(b) hydroxy,
(c) cyano,
(d) nitro,
(e) alkenyl, wherein the alkenyl moiety is optionally linked through oxygen to form a ring optionally substituted with alkyl or aryl groups on the carbon adjacent to the oxygen,
(f) substituted alkynyl
(g) hydrogen
(h) halogen,
(i) alkyl,
(j) substituted alkyl,
(k) perhalomethyl,
(l) $C_{2-6}$ alkyl,
(m) $C_{2-5}$ alkenyl,
(n) substituted ethenyl,
(o) $C_{2-3}$ alkynyl and
(p) substituted alkynyl when $R_6$ is other than amino or substituted amino;

$R_{10}$ is selected from the group consisting of:

(a) hydrogen,
(b) alkoxy,
(c) arylalkoxy,
(d) alkylthio,
(e) arylalkylthio,
(f) carboxamidomethyl,
(g) carboxymethyl,
(h) methoxy,
(i) methylthio,
(j) phenoxy and
(k) phenylthio;

Formula V

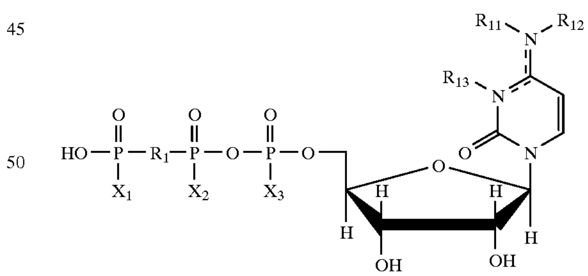

wherein:

$R_1$, $X_1$, $X_2$ and $X_3$ are defined as in Formula I;

$R_{11}$ and $R_{12}$ are H while $R_{13}$ is nothing and there is a double bond between N-3 and C-4 (cytosine); or $R_{11}$, $R_{12}$ and $R_{13}$ taken together are —CH=CH—, forming a ring from N-3 to N-4 with a double bond between N-4 and C-4 (3,$N^4$-ethenocytosine) optionally substituted at the 4- or 5-position of the etheno ring;

Formula VI

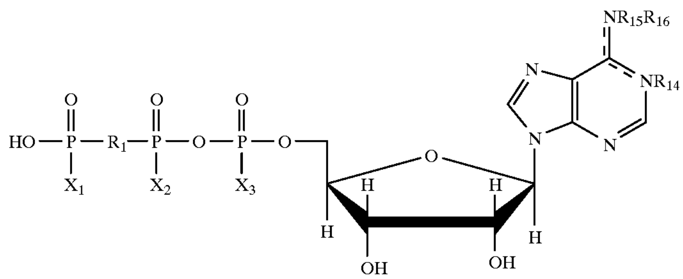

wherein:

$R_1$, $X_1$, $X_2$ and $X_3$ are defined as in Formula I;

$R_{15}$ and $R_{16}$ are H while $R_{14}$ is nothing and there is a double bond between N-1 and C-6 (adenine); or $R_{15}$ and $R_{16}$ are H while $R_{14}$ is O and there is a double bond between N-1 and C-6 (adenine 1-oxide), or $R_{15}$, $R_{16}$ and $R_{14}$ taken together are —CH═CH—, forming a ring from N-6 to N-1 with a double bond between N-6 and C-6 (1,N6-ethenoadenine).

2. A method according to claim 1, wherein said administration involves topical administration of said compound via a carrier vehicle selected from a group consisting of drops of liquid, liquid wash, gels, ointments, sprays and liposomes.

3. A method according to claim 2, wherein said topical administration comprises infusion of said compound to said ocular surface via a device selected from a group consisting of a pump-catheter system, a continuous or selective release device, and a contact lens.

4. A method according to claim 1, wherein said administration involves systemic administration of said compound by administering a liquid/liquid suspension of said compound via nose drops or nasal spray or nebulized liquid to oral or nasopharyngeal airways of said subject, such that a therapeutically effective amount of said compound contacts the lacrimal tissues of said subject via systemic absorption and circulation.

5. A method according to claim 4, wherein said systemic administration of said compound is accomplished by administering an oral form of said compound, such that a therapeutically effective amount of said compound contacts the lacrimal tissues of said subject via systemic absorption and circulation.

6. A method according to claim 4, wherein said systemic administration of said compound is accomplished by administering an injectable form of said compound, such that a therapeutically effective amount of said compound contacts the lacrimal tissues of said subject via systemic absorption and circulation.

7. A method according to claim 4, wherein said systemic administration of said compound is accomplished by administering an suppository form of said compound, such that a therapeutically effective amount of said compound contacts the lacrimal tissues of said subject via systemic absorption and circulation.

8. A method according to claim 4, wherein said systemic administration of said compound is accomplished by administering an intra-operative instillation of a gel, cream, powder, foam, crystals, liposomes, spray or liquid suspension form of said compound, such that a therapeutically effective amount of said compound contacts the lacrimal tissues of said subject via systemic absorption and circulation.

9. A method according to claim 1, wherein said compound is administered in an amount sufficient to achieve concentrations thereof on the ocular surfaces of said subject of from about $10^{-7}$ to about $10^{-1}$ moles/liter.

* * * * *

UNITED STATES PATENT AND TRADEMARK OFFICE
CERTIFICATE OF CORRECTION

PATENT NO. : 5,900,407
DATED : May 4, 1999
INVENTOR(S) : Yerxa et al.

It is certified that error appears in the above-identified patent and that said Letters Patent is hereby corrected as shown below:

Column 2,
Line 16, change "adenine" to -- adenosine --;

Columns 3 and 4,
Change
"

Formula II

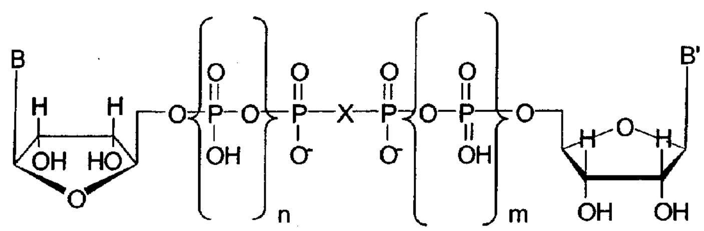

"
to --

Formula II

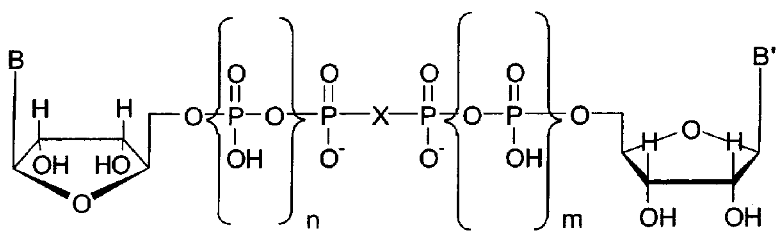

--.

Column 5,
Lines 24-25, change "R' of the 6-or 8-HNR' groups" to -- $R_1$ of the 6-$HNR_1$ group and $R_3$ --
Line 34, change "w" to -- ω --;
Line 66, change "$R^8$" to -- $R_8$ --;

Column 6,
Line 37, change "phophate" to -- phosphate --; and

UNITED STATES PATENT AND TRADEMARK OFFICE

CERTIFICATE OF CORRECTION

PATENT NO. : 5,900,407
DATED : May 4, 1999
INVENTOR(S) : Yerxa et al.

It is certified that error appears in the above-identified patent and that said Letters Patent is hereby corrected as shown below:

Column 7,
Line 32, after "in the form of", delete "the".

Column 12,
Line 9, delete the duplicate "triphosphate".
Line 35, change

"

Formula II

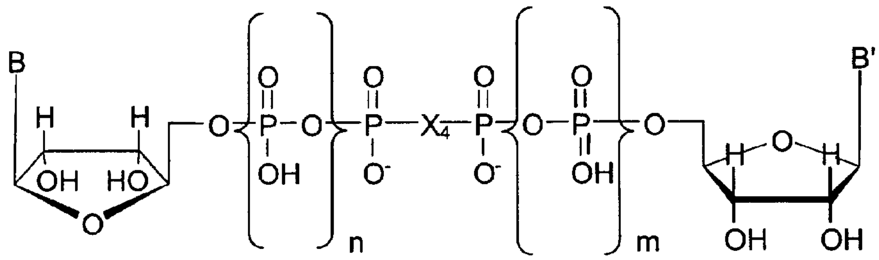

"

to --

Formula II

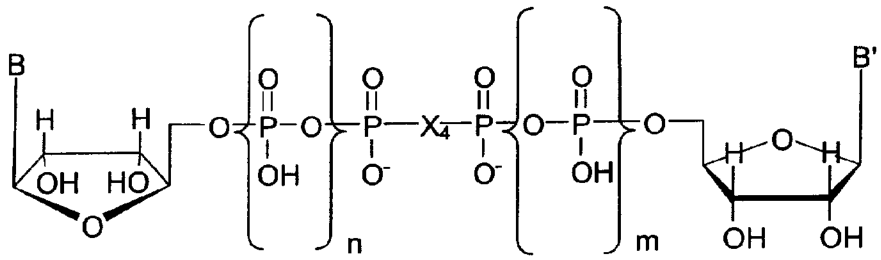

--.

Line 66, change "may for" to -- form --.
Line 67, change "1or" to -- or --.

UNITED STATES PATENT AND TRADEMARK OFFICE

CERTIFICATE OF CORRECTION

PATENT NO. : 5,900,407
DATED : May 4, 1999
INVENTOR(S) : Yerxa et al.

It is certified that error appears in the above-identified patent and that said Letters Patent is hereby corrected as shown below:

Column 13,
Lines 1, delete "of the 8-$NHR_5$ group".
Lines 14, change "(e)" to -- (g) --.
Line 65, change "forms" to -- form --.

Column 16,
Lines 27, change "an suppository" to -- a suppository --.

Signed and Sealed this

Seventeenth Day of December, 2002

JAMES E. ROGAN
*Director of the United States Patent and Trademark Office*